(12) United States Patent
Sabesan

(10) Patent No.: US 8,043,632 B2
(45) Date of Patent: Oct. 25, 2011

(54) PROCESS FOR MAKING ANTIMICROBIAL ARTICLES BY REACTING CHITOSAN WITH AMINO-REACTIVE POLYMER SURFACES

(75) Inventor: Subramaniam Sabesan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1801 days.

(21) Appl. No.: 10/919,844

(22) Filed: Aug. 17, 2004

(65) Prior Publication Data

US 2005/0118239 A1 Jun. 2, 2005

Related U.S. Application Data

(60) Provisional application No. 60/496,296, filed on Aug. 18, 2003.

(51) Int. Cl.
*A61K 9/14* (2006.01)
*A61F 2/00* (2006.01)
*A61F 13/00* (2006.01)
*C09D 5/16* (2006.01)

(52) U.S. Cl. ......... 424/488; 424/423; 424/443; 523/122

(58) Field of Classification Search .................. None
See application file for complete search history.

(56) References Cited

U.S. PATENT DOCUMENTS

| 3,864,468 | A | * | 2/1975 | Hyman et al. ................. 424/411 |
| 5,284,489 | A | * | 2/1994 | Liu et al. ........................ 606/228 |
| 5,618,622 | A | * | 4/1997 | Gillberg-Laforce et al. . 428/357 |
| 5,668,193 | A | | 9/1997 | Gouda et al. |
| 6,042,877 | A | * | 3/2000 | Lyon et al. .................... 427/2.31 |
| 6,306,835 | B1 | * | 10/2001 | Daly et al. ....................... 514/55 |
| 2003/0017194 | A1 | | 1/2003 | Joerger et al. |
| 2003/0091612 | A1 | * | 5/2003 | Sabesan ......................... 424/423 |
| 2003/0091653 | A1 | * | 5/2003 | Taylor et al. .................. 424/618 |
| 2003/0152632 | A1 | | 8/2003 | Sabesan et al. |
| 2004/0247662 | A1 | | 12/2004 | Dow et al. |
| 2005/0012630 | A1 | | 1/2005 | Misato |

FOREIGN PATENT DOCUMENTS

| JP | 5-269181 | | 10/1993 |
| JP | 2001-342435 | * | 12/2001 |
| JP | 010342435 | | 12/2001 |
| WO | WO 99/61079 | | 12/1990 |

OTHER PUBLICATIONS

Machine Translation for JP 2001-342435.*
JP 2001-342435A—Manual Translation.*
DuPont MSDS for tradekarked product "Surlyn" Revised as of Jul. 1, 2005.*
Vigo, Tyrone L., "Antimicrobial Polymers and Fibers: Retrospective and Prospective", American Chemical Society (2001) pp. 175-200.
Chirkov, S.N. "The Antiviral Activity of Chitosan (Review)", Applied Biochemistry and Microbiology, (2002), pp. 1-8, vol. 38, Russia.
International Search Report Dated: Jan. 24, 2005, International Appln. No. PCT/US2004/026797, International filing Date: Aug. 18, 2004, pp. (6).
Written Opinion of the International Searching Authority Dated: Jan. 24, 2005, International Appln. No. PCT/US2004/026797, International Filing Date: Aug. 18, 2004, pp. (6).

* cited by examiner

*Primary Examiner* — S. Tran
*Assistant Examiner* — Jeffrey T Palenik

(57) ABSTRACT

Polymer articles are rendered antimicrobial by a process that includes contacting a chitosan solution with a polymer surface that inherently contains amino-reactive functional groups as polymerized. The process requires no pretreatment with agents such as oxidizing agents or plasma to generate the necessary functional groups at the polymer surface.

6 Claims, 7 Drawing Sheets

PROCESS FOR MAKING ANTIMICROBIAL ARTICLES BY REACTING CHITOSAN WITH AMINO-REACTIVE POLYMER SURFACES

FIELD OF THE INVENTION

A process for rendering a polymer article antimicrobial comprising contacting a chitosan solution with a polymer surface that contains amino-reactive functional groups.

TECHNICAL BACKGROUND OF THE INVENTION

This invention relates to a process for rendering a polymer article antimicrobial, comprising contacting a chitosan solution with the surface of a polymer that contains amino-reactive functional groups as polymerized.

As evidenced by the presence in the market of numerous materials for eliminating or minimizing human contact with bacteria, there is clearly a demand for materials and/or processes that either minimize or kill bacteria encountered in the environment. Such materials are useful in areas of food preparation or handling and in areas of personal hygiene, such as bathrooms. Similarly, there is a use for such antibacterial materials in hospitals and nursing homes where people with lowered resistance are especially vulnerable to bacteria.

Chitosan is the commonly used name for poly-[1-4]-β-D-glucosamine. Chitosan is chemically derived from chitin, which is a poly-[1-4]-β-N-acetyl-D-glucosamine, which, in turn, is derived from the cell walls of fungi, the shells of insects and, especially, crustaceans. Thus, it is inexpensively derived from widely available materials. It is available as an article of commerce from, for example, Biopolymer Engineering, Inc. (St. Paul, Minn.); Biopolymer Technologies, Inc. (Westborough, Mass.); and CarboMer, Inc. (Westborough, Mass.).

Chitosan can be treated with metal salt solutions so that the metal ion forms a complex with the chitosan. Chitosan and chitosan-metal compounds are known to provide antimicrobial activity as bacteriocides and fungicides (see, e.g., T. L. Vigo, "Antimicrobial Polymers and Fibers: Retrospective and Prospective," in *Bioactive Fibers and Polymers*, J. V. Edwards and T. L. Vigo, eds., ACS Symposium Series 792, pp. 175-200, American Chemical Society, 2001). Chitosan is also known to impart antiviral activity, though the mechanism is not yet well understood (see, e.g., Chirkov, S. N., Applied Biochemistry and Microbiology (Translation of Prikladnaya Biokhimiya i Mikrobiologiya) (2002), 38(1), 1-8). Additionally, chitosan is known to impart antiodor properties; see, for example, WO 1999061079(A1).

Japanese Kokai 05269181 discloses the preparation of antimicrobial polymers for contact lenses and containers for contact lenses. The reference discusses chitosan being reacted with the surface of an optically clear contact lens material. Exemplified are methacrylate/carbonate copolymers with hydroxyl functionality. In one example, chitosan is attached to the surface by graft polymerization in carbodiimide aqueous solution onto an acrylic acid layer that has been first grafted onto the contact lens. In another example, a solution of chitosan in N-methyl-pyrrolidone contacts the contact lens, and the chitosan is crosslinked.

U.S. Pat. No. 5,618,622 discloses a surface-modified fibrous filtration medium which includes hydrocarbon polymer fibers having cationic or anionic functional groups on the surfaces thereof, coated with a polyelectrolyte of opposite charge, such as chitosan. There is no mention of antimicrobial properties.

Japanese patent application JP01-0342435 discloses an antimicrobial coating agent that includes both chitosan and an emulsion or aqueous dispersion of a synthetic resin selected from among copolymers which include unsaturated carboxylic acids as monomer components and ionomers obtained by partially or totally neutralizing said copolymers with metal ions. The chitosan is mixed at a ratio of about 15 to 70 parts by weight with respect to 100 parts by weight of the aforementioned synthetic resin. The surface is thus a mixture of the chitosan and the synthetic polymer. The degree of deacetylation of the chitosan is 40-55%. Its solubility in water implies that its molecular weight is low, perhaps under 10,000. This reference also teaches away from coating an acidified solution of chitosan onto a film or sheet surface.

In co-pending U.S. patent application No. 2003/0091612, polyolefin articles are treated with an aqueous mixture of chromic acid and sulfuric acid, washed with deionized water, soaked in concentrated nitric acid, and again washed with deionized water before treatment with chitosan solution. While effective antimicrobial articles are made by this method, a simpler, more economical process is desirable.

It is therefore an object of this invention to provide an antimicrobial polymeric material and a process for producing same, said process comprising contacting a chitosan solution with a polymer surface that contains amino-reactive functional groups. Also provided are articles comprising such material.

SUMMARY OF THE INVENTION

The invention discloses an antimicrobial polymeric material comprising a polymer that contains amino-reactive functional groups as polymerized and a chitosan coating wherein the chitosan is reacted with said functional groups, so that the surface of the polymeric material has a chitosan concentration of at least 1000 ppm by area.

Also disclosed are articles comprising said composition and a process for preparing said articles, said process comprising the sequential steps of:
a) providing an article whose surface comprises a polymer that inherently contains amino-reactive functional groups;
b) contacting the article with a solution comprising chitosan;
c) optionally, contacting the article of step b) with a solution containing a metal salt; and
d) drying the article produced in step b) or c).

DETAILED DESCRIPTION OF THE INVENTION

Figure 1:
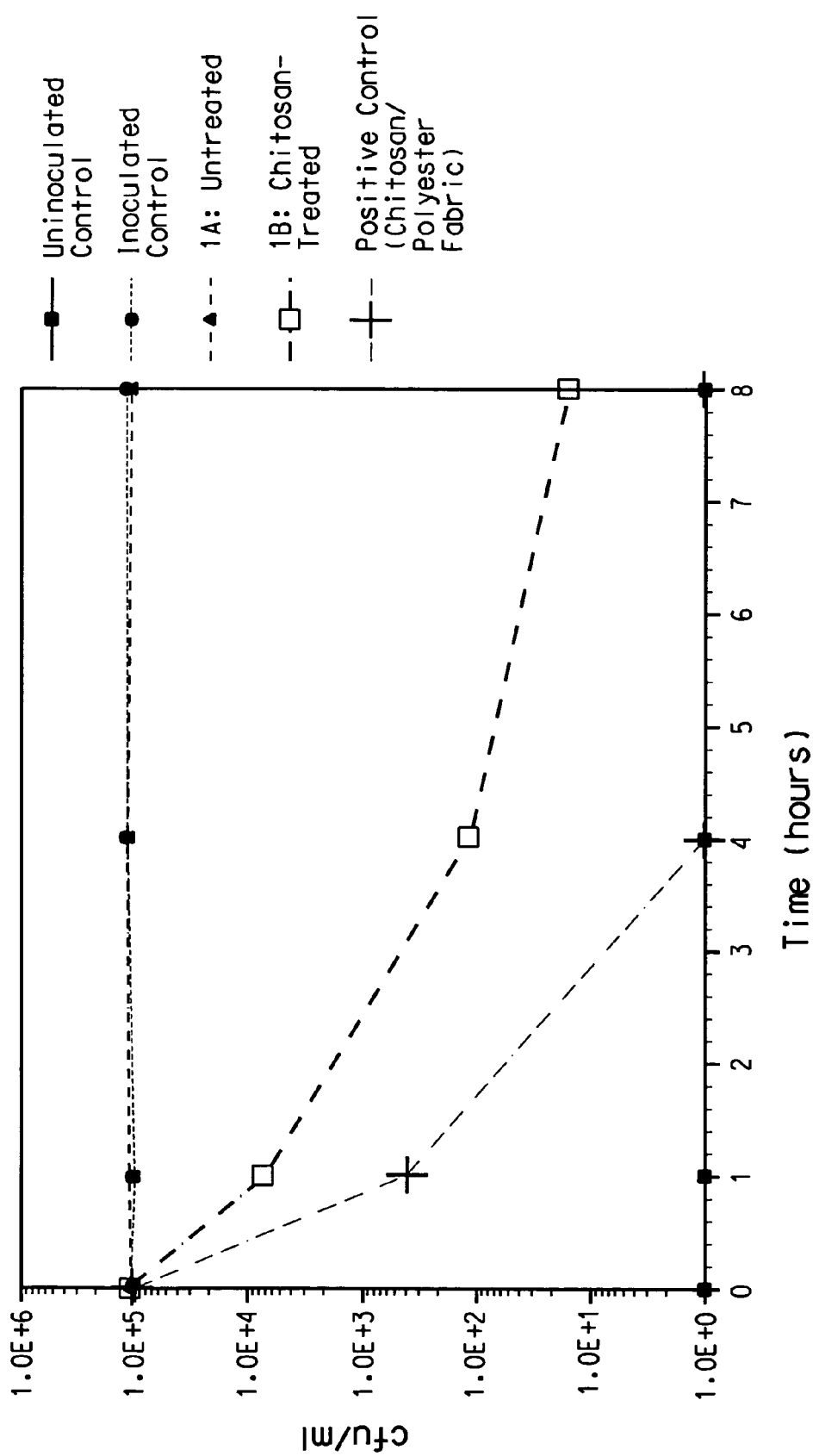
FIG. 1 is a diagram showing the antimicrobial effect of chitosan-treated, maleic anhydride-grafted low density polyethylene beads vs. *E. coli* ATCC 25922.

"Amino-reactive groups" as used herein refers to chemical functionalities that readily undergo chemical reaction with an $NH_2$ group. Examples include positively charged species such as metal ions, anhydrides, carboxylic acids, isocyanates, epoxides, acid chlorides, and enones.

The phrase "a polymer that contains amino-reactive functional groups as polymerized" as used herein refers to homopolymers and copolymers (including graft copolymers) which, as (co)polymerized, present a surface containing amino-reactive functional groups in sufficient quantity that the amino groups of the chitosan agent react with the substrate's surface to form a stable coating with a surface concentration of at least 1000 ppm chitosan, without the need for additional chemical or physical modification or priming of the substrate's surface (for example, treatment with caustic, acid, or plasma etching). Such a surface concentration of chitosan is desired for adequate antimicrobial effectiveness.

Polymer blends comprising said homopolymers and/or (co)polymers may be used in the present invention as long as the blend meets the requirement that the amino groups of the chitosan agent react with the substrate's surface to form a stable coating with a surface concentration of at least 1000 ppm chitosan.

One polymer type suitable for the present invention includes graft copolymers such as, but not limited to, those described in U.S. Pat. No. 4,026,967, in which the graft monomers include thermally stable unsaturated carboxylic anhydrides and dianhydrides, and the backbone polymers are preferably polymers of ethylene and copolymers derived from ethylene and $C_3$-$C_8$ alpha-olefins, including copolymers of at least one olefin with other monomers. Examples of suitable graft monomers for use in the present invention include methacrylic acid, acrylic acid, glycidyl methacrylate, 2-hydroxy ethylacrylate, 2-hydroxy ethyl methacrylate, diethyl maleate, monoethyl maleate, di-n-butyl maleate, maleic anhydride, maleic acid, fumaric acid, itaconic acid, itaconic anhydride, dodecenyl succinic anhydride, 5-norbornene-2,3-anhydride, and nadic anhydride (3,6-endomethylene-1,2,3,6-tetrahydrophthalic anhydride). Fumaric acid, maleic anhydride, and glycidyl methacrylate are particularly preferred graft monomers. Examples of suitable backbone polymers are polypropylene; polyethylene, e.g., high density polyethylene (HDPE), low density polyethylene (LDPE), linear low density polyethylene (LLDPE), metallocene-catalyzed polyethylene, very low density polyethylene (VLDPE), ultrahigh molecular weight polyethylene (UHMWPE), high performance polyethylene (HPPE); copolymers of ethylene and propylene; copolymers derived from ethylene or propylene and at least one monomer chosen from propylene, methyl acrylate, ethyl acrylate, n-butyl acrylate, methyl methacrylate, acrylic acid, methacrylic acid and carbon monoxide; and copolymers of olefins with a diolefin, such as a copolymer of ethylene, or of propylene, or of ethylene and other olefins, with: linear aliphatic nonconjugated dienes of at least six carbon atoms (such as 1,4-hexadiene) and other dienes, conjugated or not, such as norbornadiene, dicyclopentadiene, ethylidene norbornene, butadiene, and the like. Other suitable backbone polymers are copolymers of ethylene and tetrafluoroethylene, such as Tefzel® ETFE fluoropolymer resin available from E.I. du Pont de Nemours & Co., Inc. (Wilmington, Del.). One example of a commercially available graft copolymer suitable for use in the present invention is Bynel® 4033, a maleic anhydride grafted HDPE available from E.I. du Pont de Nemours & Co., Inc. (Wilmington, Del.).

Another type of polymer suitable for use in the present invention is a copolymer of an olefin with an acrylic and/or methacrylic acid. Ethylene is the preferred olefin. An example of a commercially available material is Nucrel® ethylene acid copolymer resin available from E.I. du Pont de Nemours & Co., Inc. (Wilmington, Del.).

Other polymers suitable for use in the present invention are ionomers. The term "ionomer" as used herein refers to a polymer with inorganic salt groups attached to the polymer chain (*Encyclopedia of Polymer Science and Technology*, 2nd ed., H. F. Mark and J. I. Kroschwitz eds., vol. 8, pp. 393-396). Two typical ionomer structures are shown below:

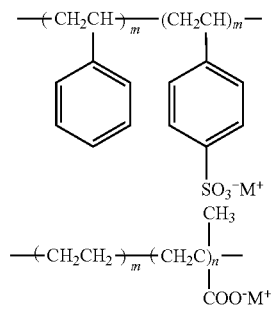

where the ratio of m to n is usually on the order of 10 to 100; that is, typically only about 1 to 9% of the repeat units contain ionic groups. Ions M are typically metal ions like lithium, sodium, lithium, or zinc but can be other cations, for example, ammonium. Typically, an acid form of the polymer is made first and then neutralized to the desired degree with base containing the desired metal ions. Partially neutralized poly(ethylene-co-methacrylic acid) and partially neutralized poly(ethylene-co-acrylic acid) are examples of ionomers, as is sulfonated polystyrene. Some examples of ionomers that have been commercialized are Surlyn® thermoplastic resin available from E.I. du Pont de Nemours & Co., Inc. (Wilmington, Del.); Nafion® perfluorinated sulfonic acid membranes, also from DuPont; Flemion® perfluorocarboxylate ionomers developed by Asahi Glass Company in Japan; and a sulfonated ethylene-propylene terpolymer from Exxon. Polyesters and polyamides that have been polymerized with a low level of sulfonated comonomer to enhance textile dyeability (see, e.g., U.S. Pat. Nos. 5,559,205; 5,607,765; and 3,389,549) and sulfonated aromatic polyamides (see, e.g., U.S. Pat. Nos. 3,567,632 and 4,595,708) such as those used in reverse osmosis membranes and other selective separation membranes are also suitable substrates for the present invention.

Examples of suitable polymer blends for use in the present invention include but are not limited to toughened grades of semicrystalline thermoplastics, such as toughened polyesters and polyamides, wherein the toughener is a polymer that contains amino-reactive groups as polymerized.

The present invention is directed to antimicrobial polymeric material and articles comprising same. Articles prepared by the methods of the invention exhibit antimicrobial functionality wherein microbial growth is reduced as the article is commonly used. The term "antimicrobial" as used herein, means bactericidal, fungicidal, and antiviral as is commonly known in the art. By "microbial growth is reduced" or "reduction of bacterial growth" is meant that a 99.9% kill of the bacteria in 24 hours has been met as measured by the Shake Flask test described below and as is commonly used to measure antimicrobial functionality which indicates a minimum requirement of a 3-log reduction in bacterial growth.

The articles of the present invention have at least one layer of chitosan reacted thereon. Chitosan is the commonly used name for poly-[1-4]-β-D-glucosamine. Chitosan is chemically derived from chitin, which is a poly-[1-4]-β-N-acetyl-D-glucosamine that, in turn, is derived from the cell walls of fungi, the shells of insects and, especially, crustaceans.

As an optional first step of the present invention, the outer surface of the article is cleaned using any method or cleaning agent commonly known in the art for the specific polymer that the article comprises. For example, the surface of a polyolefin article can be cleaned with $C_1$ to $C_6$ alcohols, dialkyl formamide and acetamide or with other polar solvents capable of extracting plasticizers. The surface of a cleaned article may then, if necessary, be dried by methods commonly known in the art, for example, by vacuum, ambient air drying, oven drying, and air forced drying.

Following the optional surface cleaning step, the article is treated with chitosan. This comprises soaking or wetting the article with a chitosan treating solution. Typically, this treating solution is an aqueous acetic acid solution, preferably about 0.5% to about 5% aqueous acetic acid. In a preferred embodiment, an aqueous solution containing 0.1% to 3% chitosan and 0.5% to 1.0% acetic acid is prepared. In more a preferred embodiment, an aqueous solution containing 2% chitosan and 0.75% acetic acid is prepared. In another preferred embodiment, 2% chitosan and 1.5% aqueous acetic acid solution is prepared. The time of treatment is typically 5 to 30 minutes. The temperature of the treatment is not critical and is typically in the range of room temperature to 90° C.

After treatment with chitosan, the article may be washed, preferably with deionized water. Optionally, the article may then be dried via methods known in the art. Such methods include ambient air drying, oven drying, and air forced drying. An inert atmosphere, such as nitrogen, may be provided in place of air. In a preferred embodiment, the articles are oven dried at about 40-90° C. for about 12 to 24 hours.

Articles prepared by the methods of the present invention exhibit antimicrobial properties and are expected to inhibit odor development as well. Said antimicrobial properties may, optionally, be further enhanced by treatment with metal salts. Metal salts useful for the present invention include, for example, zinc sulfate, copper sulfate, silver nitrate, or other water-soluble zinc, copper, and silver salts or mixtures of these. The metal salts are typically applied by dipping, spraying or padding a dilute (0.1% to 5%) solution of the salt in water onto the article.

Articles comprising the polymeric material of the present invention may be in the form of or comprise a film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of polymers are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include, but are not limited, to packaging film, liners, absorbent pads packaging, shrink bags, shrink wrap, trays, tray/container assemblies, caps, adhesives, lids, and applicators. Such absorbent pads, shrink bags, shrink wrap, and trays of the present invention are particularly useful for packaging meat, poultry, and fish.

The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to, bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging; and caps.

Examples of applicators include lipstick, chapstick, and gloss; packages and applicators for eye cosmetics, such as mascara, eyeliner, shadow, dusting powder, bath powder, blusher, foundation and creams; and pump dispensers and components thereof. These applicators are used to apply substances onto the various surfaces of the body, and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is intended to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; drains and their components; equipment for transporting water such as, but not limited to, buckets, tanks, pipes, and tubing; and machines for food cutting and slicing and components thereof. Where the surface of such equipment components is metal, a coating of a polymer containing amino-reactive groups as polymerized could first be applied to the metal surface. Alternatively, a film of such a polymer could be treated with chitosan and then heat sealed to the equipment surface. In one embodiment, the equipment component is a screw for mixing and/or conveying that is an element in a single-screw or twin-screw extruder, such as, but not limited to, an extruder used for food processing; and the polymer coating comprises an ionomer.

Articles of the present invention can also be used in or as items of apparel, such as a swimsuit, undergarment, shoe component (for example, a woven or nonwoven shoe liner or insert), protective sports pad, child's garment, or medical garment (such as a gown, mask, glove, slipper, bootie, or head covering). Such garments particularly benefit from the inhibition of odor development.

Articles of the present invention can also be used in or as medical materials, devices, or implants, such as bandages, adhesives, gauze strips, gauze pads, medical or surgical drapes, syringe holders, catheters, sutures, IV tubing, IV bags, stents, guide wires, prostheses, orthopedic pins, dental materials, pacemakers, heart valves, artificial hearts, knee and hip joint implants, bone cements, vascular grafts, urinary catheter ostomy ports, orthopedic fixtures, pacemaker leads, defibrillator leads, ear canal shunts, cosmetic implants, ENT (ear, nose, throat) implants, staples, implantable pumps, hernia patches, plates, screws, blood bags, external blood pumps, fluid administration systems, heart-lung machines, dialysis equipment, artificial skin, ventricular assist devices, hearing aids, and dental implants.

In the hygiene area, articles of the present invention include personal hygiene garments such as diapers, incontinence pads, panty liners, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy.

Additional child-oriented articles that benefit through comprising the polymeric material of the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of selective separation membranes (for example, pervaporation, dialysis, reverse osmosis, ultrafiltration, and microfiltration membranes), and air and water filters that comprise polymer with amino-reactive groups, for example, sulfonated aromatic polyamides.

The current invention is also useful in providing an antifouling surface on boat components such as, but not limited to, boat hulls and components thereof, and boat motors and components thereof. If the surface of the boat component does not comprise a polymer with amino-reactive groups as polymerized, for example, if the boat component had a metal surface, a coating of a polymer containing amino-reactive groups as polymerized could first be applied to the boat component's surface. Alternatively, a film of such polymer could be treated with chitosan and then heat sealed to the boat component's surface.

Devices used in fluid, e.g., water, transportation and/or storage can also benefit from the antimicrobial polymeric material of the invention. Exemplary devices include, but are not limited to, pipes and tanks. The inner surface, outer surface, or both surfaces of a pipe or tank can comprise an antifouling surface of the invention. If the surface(s) does not comprise a polymer with amino-reactive groups as polymerized, for example, if the surface(s) had a metal surface, a coating of a polymer containing amino-reactive groups as polymerized could first be applied to the surface(s). Alternatively, a film of such polymer could be treated with chitosan and then heat sealed to the surface(s).

In order to impart antimicrobial functionality to the products listed, the product can be treated with a chitosan agent according to the method of the invention before it is manufactured, or after, or at any time during manufacture of the product. For example, in making an antimicrobial shower curtain, material having a surface that comprises an effective amount of amino-reactive polymer can be treated according to the method of the invention, followed by fashioning a shower curtain from the treated material. Alternatively, the chitosan treatment may be performed after the material is made into a shower curtain. It is believed that the antimicrobial properties of the material will not change significantly.

EXAMPLES

The present invention is further defined in the following Examples, in which all parts and percentages are by weight and degrees are Celsius. It should be understood that these Examples, while indicating preferred embodiments of the invention, are given by way of illustration only. From the above discussion and these Examples, one skilled in the art can ascertain the essential characteristics of this invention, and, without departing from the spirit and scope thereof, can make changes and modifications to adapt the invention to various usages and conditions.

Materials and Methods:

The chitosan used in this study was material commercially available under the registered trademark ChitoClear® from Primex Corporation of Norway. The material was used as purchased.

The degree of N-deacetylation of the chitosan samples was ascertained by proton and carbon 13 NMR spectroscopy to be over 85%. The molecular weight of the samples ranged from approximately 70,000 to approximately 350,000.

Treated articles were tested for antimicrobial properties by the Shake Flask Test for Antimicrobial Testing of Materials using the following procedure:

1. Inoculate a single, isolated colony from a bacterial or yeast agar plate culture in 15-25 ml of Trypticase Soy Broth (TSB) in a sterile flask. Incubate at 25-37° C. (use optimal growth temperature for specific microbe) for 16-24 h with or without shaking (select appropriate aeration of specific strain). For filamentous fungi, prepare sporulating cultures on agar plates.

2. Dilute the overnight bacterial or yeast culture into sterile phosphate buffer (see below) at pH 6.0 to 7.0 to obtain approximately $10^5$ colony forming units per ml (cfu/ml). The total volume of phosphate buffer needed will be 50 ml×number of test flasks (including controls). For filamentous fungi, prepare spore suspensions at $10^5$ spores/ml. Spore suspensions are prepared by gently resuspending spores from an agar plate culture that has been flooded with sterile saline or phosphate buffer. To obtain initial inoculum counts, plate final dilutions (prepared in phosphate buffer) of $10^{-4}$ and $10^{-3}$ onto Trypticase Soy Agar (TSA) plates in duplicate. Incubate plates at 25-37° C. overnight.

3. Transfer 50 ml of inoculated phosphate buffer into each sterile test flask containing 0.5 g of material to be tested. Also, prepare control flasks of inoculated phosphate buffer and uninoculated phosphate buffer with no test materials.

4. Place all flasks on a wrist-action shaker and incubate with vigorous shaking at room temperature. Sample all flasks periodically and plate appropriate dilutions onto TSA plates. Incubate at 25 to 37° C. for 16 to 48 h and count colonies.

5. Report colony counts as the number of Colony Forming Units per ml (cfu/ml).

6. The Δt value may be calculated as follows: Δt=C−B, where Δt is the activity constant for contact time t, C is the mean $\log_{10}$ density of microbes in flasks of untreated control materials after X hours of incubation, and B is the mean $\log_{10}$ density of microbes in flasks of treated materials after X hours of incubation. Δt is typically calculated at 4, 6, or 24 hours and may be expressed as $\Delta t_X$.

Stock Phosphate Buffer:

| | |
|---|---|
| Monobasic Potassium Phosphate: | 22.4 g |
| Dibasic Potassium Phosphate: | 56.0 g |
| Deionized Water: | Bring up volume to 1000 ml |

Adjust the pH of the phosphate buffer to pH 6.0 to 7.0 with either NaOH or HCl, filter, sterilize, and store at 4° C. until use. The working phosphate buffer is prepared by diluting 1 ml of stock phosphate buffer in 800 ml of sterile deionized water.

Example 1

Preparation and Antimicrobial Evaluation of Chitosan and Chitosan-Silver Treated Maleic Anhydride-Grafted Polyethylene Beads Low density polyethylene beads grafted with maleic anhydride (50 g, metallocene-catalyzed VLDPE, 2 Ml, 0.5% maleic anhydride graft) were heated with 2% chitosan (Primex ChitoClear TM 1111, m.wt. 350,000) solution in 0.75% aqueous acetic acid (200 ml) at 80° C. for 30 minutes, cooled, filtered, and washed with deionized water. It was then dried at 80° C. for 16 h. (Sample 1B).

Sample 1B (2 g) was immersed in 2% aqueous silver nitrate solution (10 ml) and gently shaken for 30 min. The beads were then filtered and washed three times with deionized water and dried under nitrogen at 40° C. (Sample 1C). These beads (1B and 1C) were evaluated for their antibacterial properties against E. coli ATCC 25922, where ATTC refers to the American Type Culture Collection, and E. coli O157:H7, compared with untreated polymer beads (Sample 1A) and, as a positive control, a chitosan-treated poly(ethylene terephthalate) fabric. This fabric was sequentially treated with 3% aqueous sodium hydroxide at 93° C. for 30 min., neutralized with acetic acid, acidified with aqueous hydrochloric acid (pH 1.0), washed with water, and finally treated with chitosan solution (chitosan (Primex ChitoClear TM 588, m. wt, about 70,000, 2% in 1% aqueous acetic acid solution), followed by drying the fabric at 77° C. for 8 h.

Figure 2:
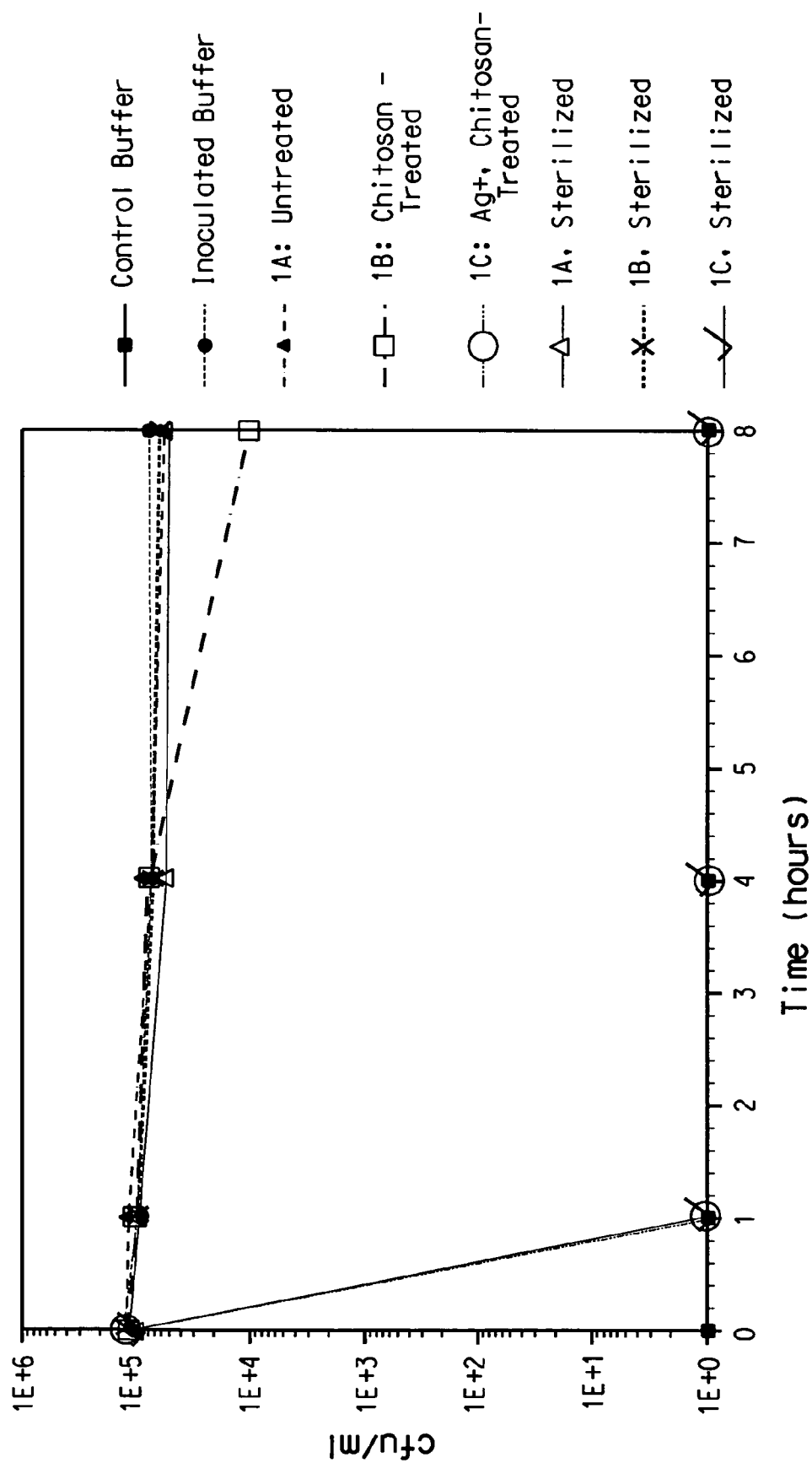
FIG. 2 is a diagram showing the antimicrobial effect of chitosan-treated, maleic anhydride-grafted low density polyethylene beads vs. *E. coli* O157:H7, with and without silver doping.

Samples of 1A, 1B, and 1C were also autoclaved with steam at 121° C. for 20 minutes to sterilize them. The sterilized beads were then evaluated for antibacterial effectiveness. Results are shown in FIGS. 1 and 2. Untreated beads were not effective, chitosan treated ones were very slightly effective, and silver plus chitosan treated, most effective. Antibacterial effectiveness remained after sterilization.

Example 2

Preparation and Antimicrobial Evaluation of Antimicrobial Maleic Anhydride-Grafted High Density Polyethylene Beads High density polyethylene beads grafted with maleic anhydride (50 g, Bynel® 4033) were heated with 2% chitosan (Primex ChitoClear® TM 1111, m.wt. 350,000) solution in 0.75% aqueous acetic acid (200 ml) at 80° C. for 30 minutes, cooled, filtered, and washed with deionized water. It was then dried at 80° C. for 16 h. (Sample 2A).

Figure 3:
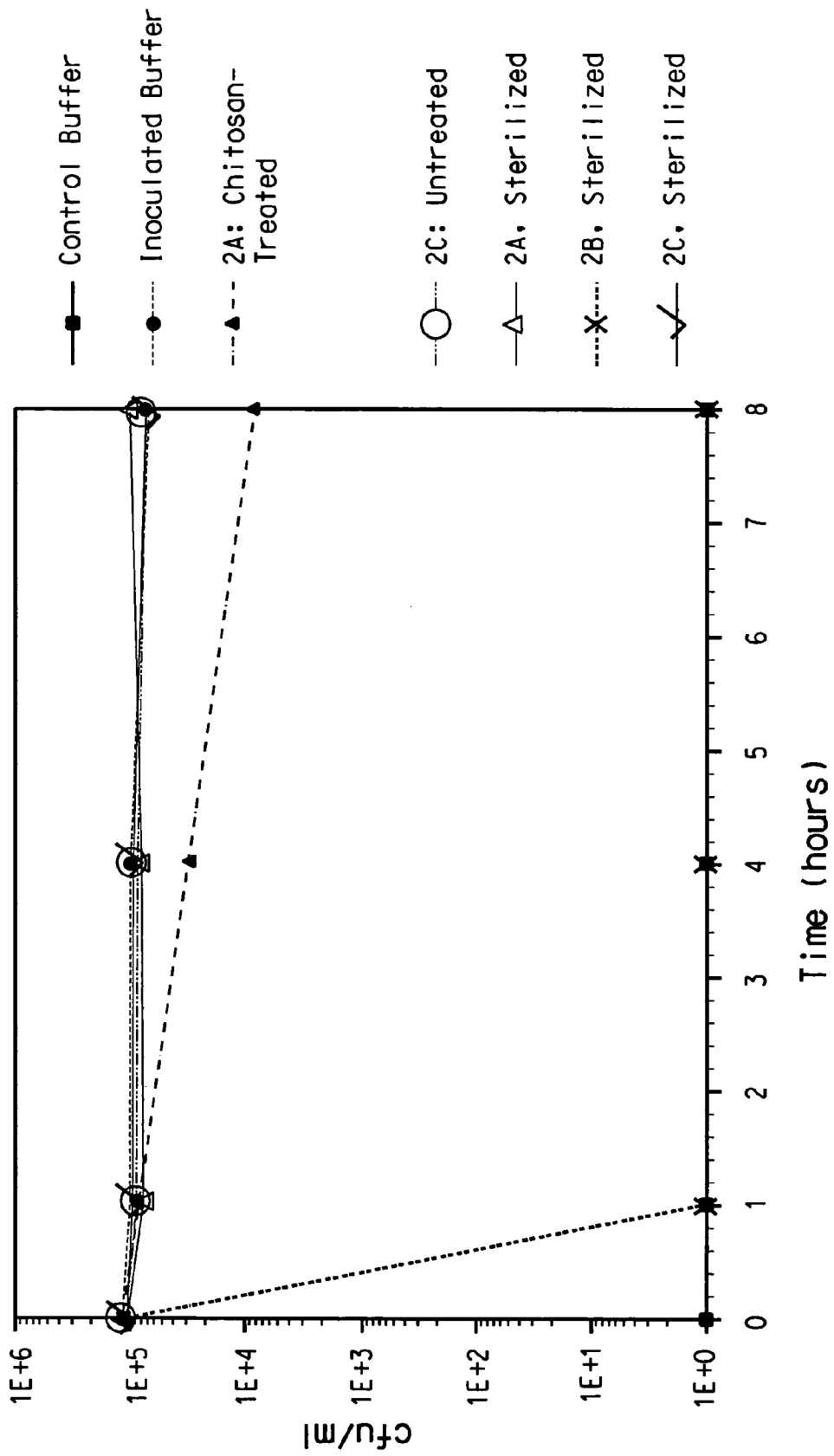
FIG. 3 is a diagram showing the antimicrobial effect of chitosan-treated, maleic anhydride-grafted high density polyethylene beads vs. *E. coli* O157:H7, with and without silver doping.

Sample 2A (10 g) was immersed in 2% aqueous silver nitrate solution (50 ml) and gently shaken for 30 min. The beads were then filtered and washed three times with deionized water and dried under nitrogen at 40° C. (Sample 2B). Samples 2A, 2B, and untreated beads (2C) were evaluated for their antibacterial properties against E. coli O157:H7. Beads of 2A, 2B, and 2C that had been sterilized by autoclaving at 125° C. were also evaluated for antimicrobial activity. Results are shown in FIG. 3. Silver/chitosan treatment was most effective, and the antimicrobial activity of the silver/chitosan-treated beads was retained after sterilization.

Example 3

Figure 4:
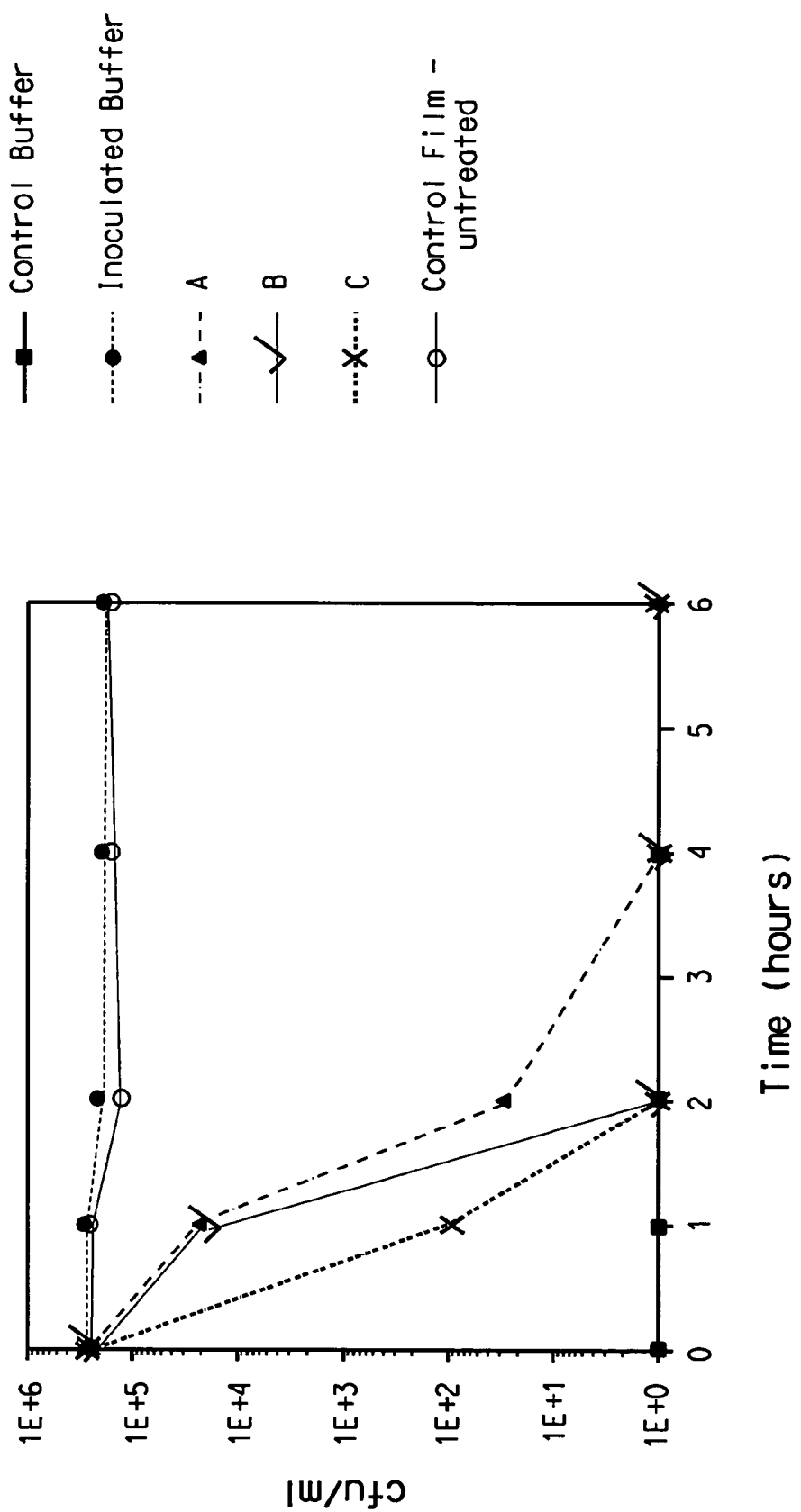
FIG. 4 is a diagram showing the antimicrobial effect of chitosan-treated, maleic anhydride-grafted low density polyethylene films vs. *E. coli* ATCC 25922.

Preparation and Antimicrobial Evaluation of Chitosan-Treated Maleic Anhydride-Grafted Polyethylene Films Polyethylene film grafted on one side with maleic anhydride at a level of 1 wt % was soaked in a solution of 2% chitosan (Primex ChitoClear® TM 588, m.wt. 70,000) in aqueous 1.5% acetic acid for 30 min, air dried, then cured at 60° C. under nitrogen for 16 h. Three pieces of the film, samples A, B, and C, were evaluated for antimicrobial efficacy against E. coli ATCC 25922 in a shake flask test. Results are shown in FIG. 4.

Example 4

Preparation of Nucrel®/Chitosan and Surlyn®/Chitosan Films and Antibacterial Evaluation Two film samples (A, B) each of Nucrel® 0403 ethylene-methacrylic acid copolymer (typical methacrylic acid content of 4.0%), Nucrel® 0903 ethylene-methacrylic acid copolymer (typical methacrylic acid content of 9.0%), Surlyn® 1601 packaging resin (sodium ionomer, typical melt flow index 1.3 dg/min by ASTM D1238, condition 190° C./2.16 kg), and Surlyn® 1702 packaging resin (zinc ionomer, melt flow index 14.0 dg/min. by ASTM D1238, condition 190° C./2.16 kg) were weighed, soaked in 1 M aqueous hydrochloric acid for 30 min., washed with water, and then soaked in 2% chitosan solution (Primex ChitoClear® TM 656 in 0.5% aqueous acetic acid) overnight. The films were removed, the excess chitosan was allowed to drip off, and finally the films were dried at 60° C. under nitrogen atmosphere for 48 h. and re-weighed, as indicated in Table 1. It is thought that the few zero or negative weight gains are due to experimental uncertainty and/or dehydration of an initially hydrated sample by the chitosan treatment.

TABLE 1

| Sample | Initial Film Weight (g) | Weight After Chitosan Treatment (g) | Weight gain (g) |
| --- | --- | --- | --- |
| Surlyn ® 1601 (A) | 5.90 | 5.96 | 0.06 |
| Surlyn ® 1601 (B) | 5.80 | 5.87 | 0.07 |
| Surlyn ® 1702 (A) | 5.63 | 5.62 | −0.01 |
| Surlyn ® 1702 (B) | 5.62 | 5.62 | 0.00 |
| Nucrel ® 0903 (A) | 5.84 | 5.90 | 0.06 |
| Nucrel ® 0903 (B) | 5.85 | 5.91 | 0.06 |
| Nucrel ® 0403 (A) | 2.94 | 2.98 | 0.04 |
| Nucrel ® 0403 (B) | 2.94 | 2.86 | −0.08 |

Figure 5:
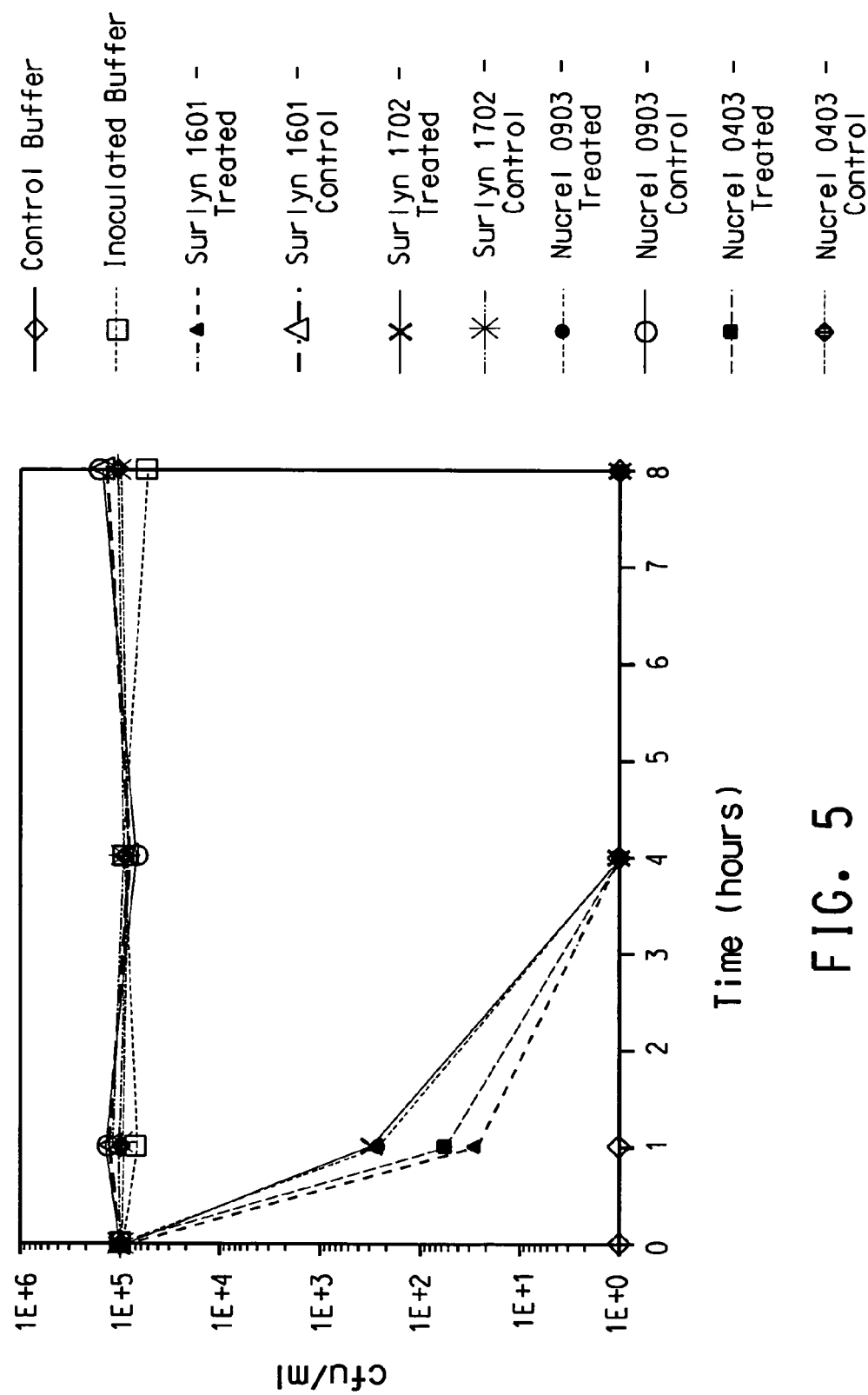
FIG. 5 is a diagram showing the antimicrobial effect of chitosan-treated films of Surlyn® thermoplastic resin and Nucrel® ethylene acid copolymer vs. *E. coli* ATCC 25922.

The chitosan-treated B films were tested for antimicrobial properties against *E. coli* ATCC 25922 as described above, along with the corresponding untreated films as controls. Results are shown in FIG. 5.

Example 5

Preparation of Nafion®-Chitosan Film and Antibacterial Evaluation

Figure 6:
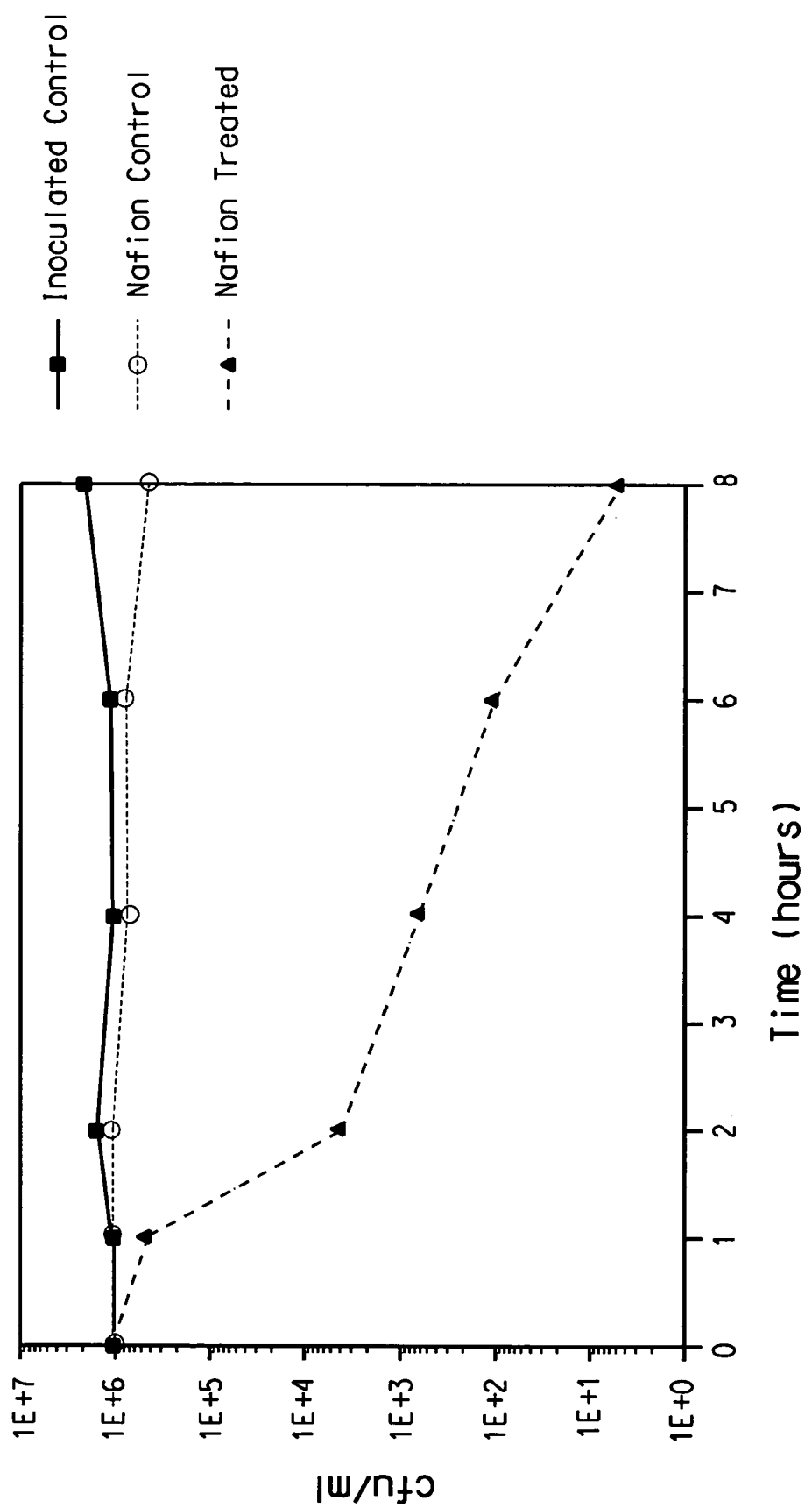
FIG. 6 is a diagram showing the antimicrobial effect of chitosan-treated Nafion® 117 film vs. *E. coli* ATCC 25922.

A piece of Nafion® 117 perfluorosulfonic acid polymer film (about 183 microns thick, weighing 10.91 g) was soaked in 2% chitosan solution (ChitoClear®, Primex TM 588, m.wt. about 70,000, in 1.5% aqueous acetic acid) for 5 min, air dried, followed by drying under nitrogen at 80° C. Weight of the dried film was 10.91 g. The lack of a net weight gain was most likely due to dehydration of the initially highly hydrated Nafion® 117 film by the chitosan treatment. This was evaluated for antibacterial activity against *E. coli* ATCC 25922 as described above, as was a control film of untreated Nafion® 117 film. Results are shown in FIG. 6. The chitosan-treated Nafion® 117 film provided a 2.6 log reduction of *E. coli* ATCC 25922 population after 2 hours, a 3.2 log reduction after 4 hours, a 4.0 log reduction after 6 hours, and a 5.6 log reduction after 8 hours. In contrast, the untreated Nafion® 117 film did not demonstrate antimicrobial activity.

Example 6

Figure 7:
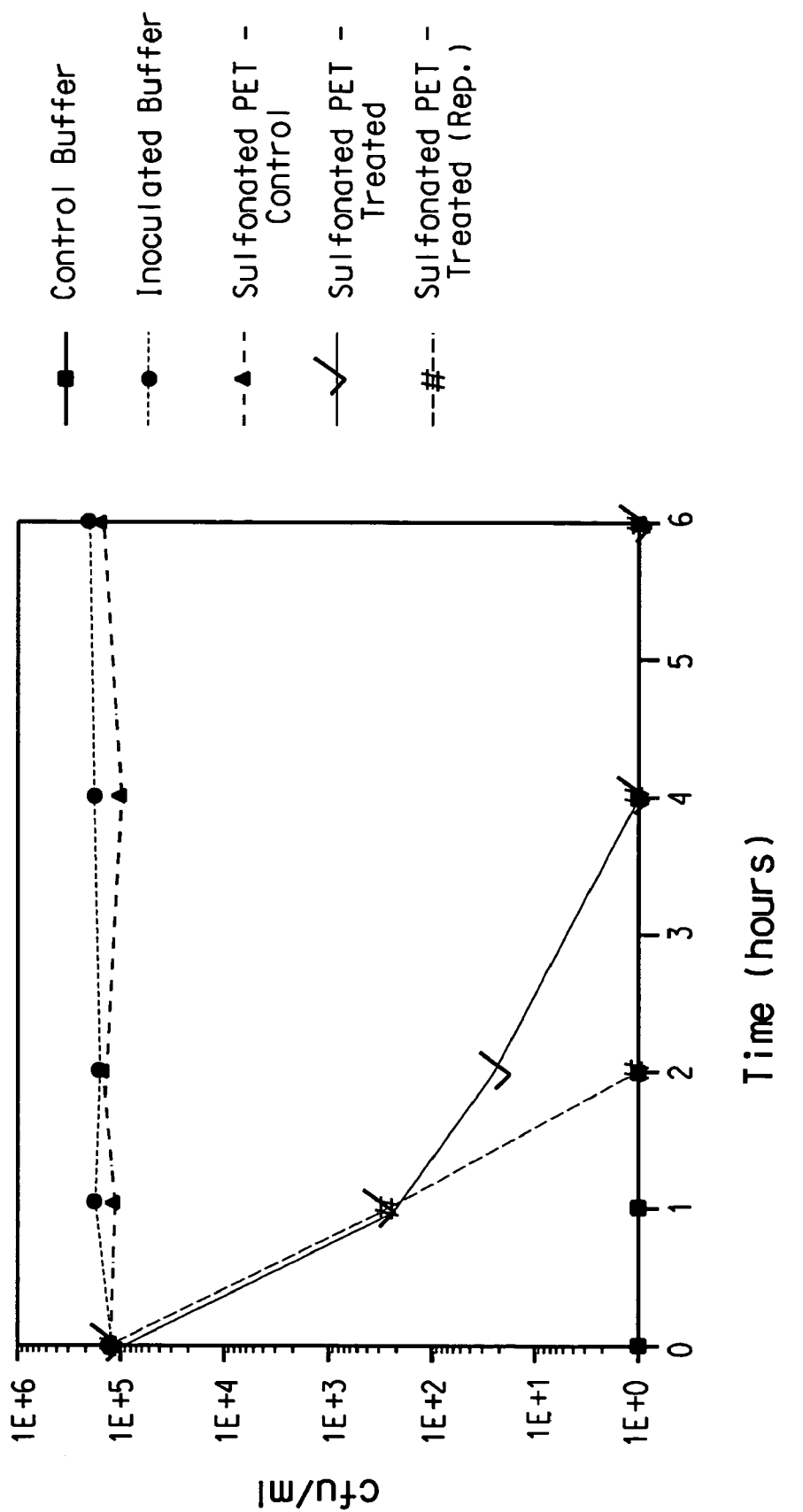
FIG. 7 is a diagram showing the antimicrobial effect of chitosan-treated sulfonated polyester yarn vs. *E. coli* ATCC 25922.

Preparation of Antimicrobial Sulfonated Polyester Yarn and Antibacterial Evaluation Yarn made from poly(ethylene terephthalate) that had been copolymerized with a lithium salt of a glycollate of 5-sulfo-isophthalic acid at of a level of approximately 1.75 mol % based on total diacids was passed sequentially through a tray containing water and a tray containing 2% chitosan solution (Primex ChitoClear® TM 588, m.wt. about 70,000, in 1.5% aqueous acetic acid). The excess solution was stripped off, and the yarn was dried with a roller heated to 200° C. The wound yarn was subsequently dried at 80° C. for a few days. Two samples (replicates) were taken and submitted for antimicrobial activity evaluation. Both demonstrated antimicrobial activity against *E. coli* ATCC 25922, as shown in FIG. 7.

What is claimed is:

1. A polymeric material comprising
   a) a polymer that as polymerized, presents a surface that contains amino-reactive functional groups, wherein the amino-reactive functional groups are metal ions, ammonium ions, anhydrides, carboxylic acids, sulfonic acid, isocyanates, epoxides, acid chlorides, enones, and combinations thereof; wherein the polymer is provided in the form of film or yarn, wherein said surface has not been subjected to chemical or physical modification or priming by treatment with caustic, acid or plasma etching prior to contacting the surface with a chitosan solution to form a chitosan coating;
   b) a chitosan coating on the surface of the polymer, wherein the chitosan coating is formed by contacting the surface with a chitosan solution such that the chitosan is reacted with said functional groups and then drying the chitosan coating, and wherein the surface of said polymeric material has a chitosan concentration sufficient to reduce microbial growth; and
   c) one or more metal salts wherein the metal salt has been applied by dipping, spraying or padding a dilute solution consisting of the salt in water onto the dried chitosan-coated surface of the polymeric material.

2. The polymeric material of claim 1, wherein the polymer is a homopolymer, random copolymer, block copolymer, graft copolymer, or polymer blend, at least one monomer or comonomer of which contains at least one functional group selected from the group consisting of metal ions, ammonium ion, anhydrides, carboxylic acid or carbonate, sulfonic acid or sulfonate, isocyanates, epoxides, acid chlorides, and enones.

3. The polymeric material of claim 1, wherein the polymer material comprises an ionomer.

4. The polymeric material of claim 3, wherein the ionomer is an ionomer of ethylene/acrylic acid copolymer or of ethylene/methacrylic acid copolymer; a perfluorinated sulfonate or carboxylate polymer; a sulfonated polystyrene; a sulfonated ethylene-propylene terpolymer; a sulfonated polyester; or a sulfonated polyamide.

5. The polymeric material of claim 1, wherein the polymer is a copolymer of ethylene with acrylic acid or methacrylic acid.

6. The polymeric material of claim 1, wherein the metal salts are selected from water-soluble zinc salt, water-soluble copper salt, water-soluble silver salt, and mixtures thereof.

* * * * *